(12) United States Patent
Lee

(10) Patent No.: US 11,684,639 B2
(45) Date of Patent: *Jun. 27, 2023

(54) PHARMACEUTICAL COMPOSITION FOR PREVENTING AND TREATING CELL PROLIFERATIVE DISEASE COMPRISING MIXTURE OF FEATHER OF BIRDS AND SCALE OF FISH AS AN ACTIVE INGREDIENT

(71) Applicant: Sang-Moon Lee, Seongnam-si (KR)

(72) Inventor: Sang-Moon Lee, Seongnam-si (KR)

(73) Assignee: Sang-Moon Lee, Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/996,201

(22) Filed: Aug. 18, 2020

(65) Prior Publication Data

US 2021/0085726 A1   Mar. 25, 2021

Related U.S. Application Data

(62) Division of application No. 15/229,028, filed on Aug. 4, 2016, now Pat. No. 10,744,165, which is a division of application No. 12/673,676, filed as application No. PCT/KR2008/004675 on Aug. 12, 2008, now abandoned.

(30) Foreign Application Priority Data

Aug. 16, 2007 (KR) .................. 10-2007-0082401

(51) Int. Cl.
| | | |
|---|---|---|
| *A61K 35/57* | (2015.01) | |
| *A61K 35/60* | (2006.01) | |
| *A61K 35/12* | (2015.01) | |
| *A61K 9/00* | (2006.01) | |
| *A61K 35/58* | (2015.01) | |

(52) U.S. Cl.
CPC ............ *A61K 35/57* (2013.01); *A61K 9/0053* (2013.01); *A61K 35/12* (2013.01); *A61K 35/58* (2013.01); *A61K 35/60* (2013.01)

(58) Field of Classification Search
None
See application file for complete search history.

(56) References Cited

U.S. PATENT DOCUMENTS

2006/0240117 A1   10/2006   Lecca
2011/0111045 A1*   5/2011   Lee .................. A61K 35/58
                                                      424/520

FOREIGN PATENT DOCUMENTS

| DE | 3610555 A1 | 10/1987 |
|---|---|---|
| JP | 2011-139985 A | 5/1999 |
| JP | 2002-308789 A | 10/2002 |
| JP | 2003-023970 A | 1/2003 |
| JP | 2005-306761 A | 11/2005 |
| KR | 2010-2005-0122083 A | 12/2005 |
| WO | 2009/022842 A2 | 2/2009 |

OTHER PUBLICATIONS

Wright (2007) Cytotoxic Chemotherapy. In The Biology of Cancer, edited by Janice Ann Gabriel, John Wiley & Sons, Inc. pp. 45-53 (year: 2007).
Website document entitled "Drugs Approved for Different Types of Cancer" (available at https://www.cancer.gov/about-cancer/treatent/drugs/cancer-type). Download from website Jun. 26, 2019 (Year: 2019).
De Vita et al. (1975) Cancer 35: 98-110. (Year: 1975).
Raskin et al. (2004) Current Pharmaceutical Design, 10, 3419-3429. (Year: 2004).
Yoshinori, "Possibility of Collagentight", New Food Industry, 48(12):45-62, 2006, English Abstract.
Yazawa, "Functionality of Marin Vitamin and its application," Japan Food Science, 40(12): 61-68, 2001, English Abstract.
International Search Report from counterpart PCT application PCT/KR2008/004675 dated Mar. 11, 2009.

* cited by examiner

*Primary Examiner* — Russell G Fiebig
(74) *Attorney, Agent, or Firm* — FisherBroyles, LLP; Joseph Hyosuk Kim

(57) ABSTRACT

The present invention relates to a pharmaceutical composition for preventing and treating cell proliferative diseases comprising a feather of birds and a scale of fish, a scale transformed from the dermis, a degenerated or cornified variant of a scale, or a scale or horny scale of reptiles as an active ingredient. More particularly, the present invention relates to a pharmaceutical composition for preventing and treating cell proliferative diseases comprising a mixture of 70~85 weight % of a feather of birds and 15~30 weight % of a scale of fish, a scale transformed from the dermis, a degenerated or cornified variant of a scale, or a scale or horny scale of reptiles as an active ingredient. The inventive composition has the effect of inhibiting and preventing growth of cancer cells. Accordingly, the inventive composition may be used for anticancer purposes to prevent, ameliorate or treat cancer.

16 Claims, 1 Drawing Sheet

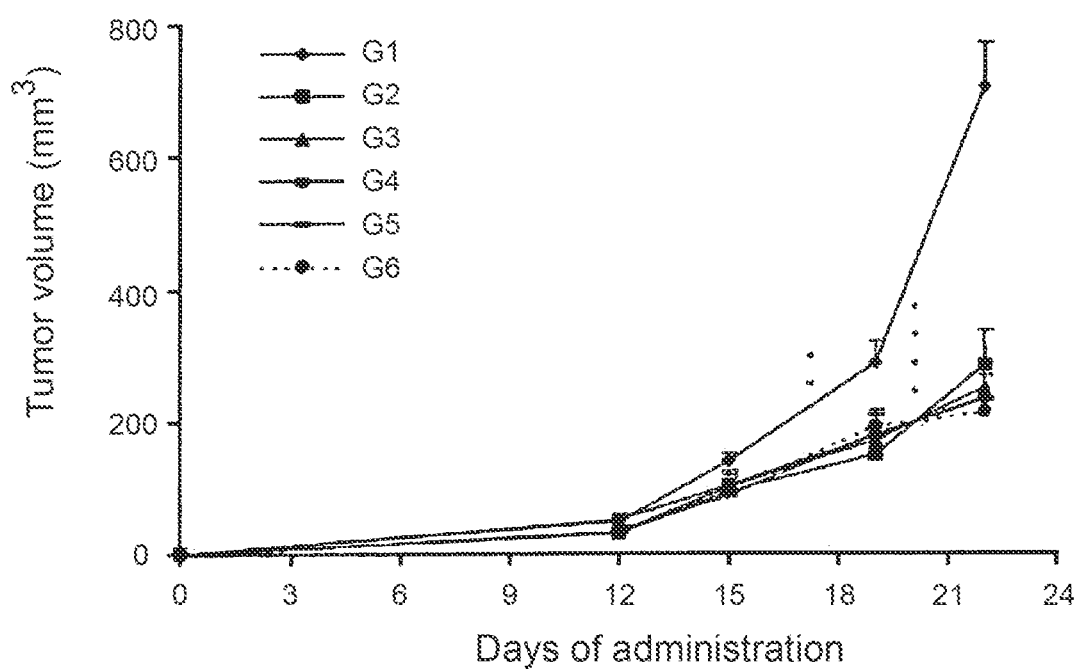

PHARMACEUTICAL COMPOSITION FOR PREVENTING AND TREATING CELL PROLIFERATIVE DISEASE COMPRISING MIXTURE OF FEATHER OF BIRDS AND SCALE OF FISH AS AN ACTIVE INGREDIENT

TECHNICAL FIELD

The present invention relates to a pharmaceutical composition for preventing and treating cell proliferative diseases comprising feather of birds and a scale of fish, a scale transformed from the dermis, a degenerated or cornified variant of a scale, or a scale or horny scale of reptiles as an active ingredient. More particularly, the present invention relates to a pharmaceutical composition for preventing and treating cell proliferative diseases comprising a mixture of 70~85 weight % of feather of birds and 15~30 weight % of a scale of fish, a scale transformed from the dermis, a degraded or cornified variant of a scale, or a scale or horny scale of reptiles as an active ingredient.

BACKGROUND ART

Cancer is a class of diseases resulting from uncontrolled proliferation and non-systemic growth of transformed cells. Mostly, cancers are caused by mutations in oncogenes and tumor suppressor genes which occur due to environmental, genetic or other causes. In the early stages, cancer cells proliferate and invade and destroy nearby tissues. In the later stages, they invade the circulatory system and spread to distant areas, ultimately resulting in the death of the victim.

In order to treat cancers, surgeries, radiotherapies, chemotherapies, and the like are applied, and various substances known to have anticancer effect are used. Although most chemical anticancer agents exhibit the effect of controlling cell growth, they are without selectivity for cancer cells and tend to show toxicity to normal cells. Accordingly, development of new anticancer agents which provide superior selectivity cancer cells, have less toxicity and are capable of overcoming resistance is needed.

Feathers are one of the epidermal variants that form the distinctive outer covering on birds. The major component of a feather is keratin. Embryologically, it corresponds to the hair of mammals or the scale of reptiles. The feather of birds consists of a calamus (or hollowshaft) which inserts into a follicle in the skin, a rachis which is connected to the calamus and serves as the main shaft, and a plurality of barbs which are branched from the rachis. Small barbs are entangled with each other to form a vane. In general, a feather has brown or black melanin pigments and thus has a color.

Typically, it is composed of fibrous hard proteins insoluble in water or aqueous salt solution. The feather is derived from the bone and is rich in calcium. Connected by calcium chains, the feather is air-permeable and structurally adequate for flying.

The scale of fish refers to a small rigid plate that covers the skin of fish. The scale of fish is derived from the dermis (consisting of connective tissue). It has various shapes and numbers depending on species. For instance, the numbers of vertically aligned are 33 for a carp, 27 for a crucian carp, 150 for a salmon, and 118 for a trout. The chemical composition of a scale is 41~84% of dry organic components and about 59% of ash components. Most of the organic components are hard protein collagen (24%) and lepidin (76%). As for a carp, the ash components account for 29.58%. They are $Ca_3(PO_4)_2$ (51.42%), $Mg_3(PO_4)_2$ (6.45%) and $CaCO_3$ (42.17%). The contents of calcium phosphate and calcium carbonate are almost the same. The scales are obtained as byproduct during the processing of fish, but are mostly discarded. Some of them are powdered after heating for use as feed or fertilizer.

The inventors of the present invention have carried out researches to find substances from natural products that can prevent and inhibit proliferation of cancer cells. As a result, we have found that a composition comprising a feather of birds, particularly a calamus and a rachis, and a scale of fish, a scale transformed from the dermis, a degenerated or cornified variant of a scale, or a scale or horny scale of reptiles has superior anticancer effect and completed the present invention.

DISCLOSURE

Technical Problem

Accordingly, an object of the present invention is to provide a composition for preventing and treating cell proliferative diseases.

Technical Solution

In order to attain the aforesaid object, in an aspect, the present invention provides a composition for preventing and treating cell proliferative diseases comprising feather of birds and a scale of fish, a scale transformed from the dermis, a degenerated or cornified variant of a scale, or a scale or horny scale of reptiles in the form of powder.

In another aspect, the present invention provides a method for preparing a powder of a feather of birds.

In another aspect, the present invention provides a method for preparing a powder of a scale of fish.

In another aspect, the present invention provides a method for preparing a powder of scale transformed from the dermis, or the like.

In another aspect, the present invention provides a method for orally administering the composition of the present invention.

Advantageous Effects

The inventive composition for preventing and treating cell proliferative diseases has the effect of inhibiting and preventing growth of cancer cells. Accordingly, the inventive composition for preventing and treating cell proliferative diseases may be for anticancer purposes to prevent, ameliorate or treat cancer.

DESCRIPTION OF DRAWINGS

The above and other objects, features and other advantages of the present invention will be more clearly understood from the following detailed description taken in conjunction with the accompanying drawings, in which:

FIG. 1 is a graph showing the change of the tumor volume of a nude mouse in which human colon cancer cells (HCT-15) were transplanted, where G1: control
G2: doxorubicin, 2 mg/kg
G3: inventive anticancer composition, 75 mg/kg
G4: inventive anticancer composition, 150 mg/kg
G5: inventive anticancer composition, 300 mg/kg
G6: inventive anticancer composition, 300 mg/kg (pretreated)

BEST MODE

Hereinafter, the present invention is described in more detail.

The pharmaceutical composition of the present invention is characterized by comprising a powder of a feather of birds and a scale of fish, a scale transformed from the dermis, a degenerated or cornified variant of a scale, or a scale or horny scale of reptiles as an active ingredient.

The feather of birds used to prepare the pharmaceutical composition of the present invention is not particularly limited. But, preferably, a feather of chicken, duck, turkey, goose or ostrich may be used. More preferably, a feather of chicken may be used.

As described above, a feather of birds comprises a calamus, a rachis and barbs. The feather of birds may be used as a whole. But, preferably, only the calamus and the rachis of the feather of birds may be used. In particular, the portion of the feather of birds which exhibits color includes a lot of brown or black melanin pigments. According to experiments, the compositions including these portions exhibited superior effect. Therefore, it is preferred to use the portion containing a lot of melanin pigments.

The separation of the calamus, the rachis and the portions containing a lot of melanin pigments from the feather of birds can be carried out without particular limitation. Preferably, they may be separated by hydrating the feather of birds by immersing in water followed by applying physical force, for example, using a knife.

The water used for immersing the feather is not particularly limited. Preferably, common tap water or distilled water may be used, and one having a temperature from 20° C. to 77° C. is preferable. If the water temperature exceeds 77° C., the epidermal tissue may be deformed. And, if the water temperature is below 20° C., hydration may be insufficient. The immersing time may be controlled depending on the condition of the materials so as to attain sufficient hydration. Preferably, the immersing time may be from 1 minute to 2 hours. If the immersing time is less than 1 minute, hydration may be insufficient. And, an immersing time exceeding 2 hours is uneconomical and may result in deformation of tissues.

The pharmaceutical composition of the present invention comprises a powder of a whole feather of birds or of a calamus or rachis of a feather of birds prepared by the steps of: (a) immersing a feather of birds in water of 20° C.~77° C. for 1 minute to 2 hours. (b) sterilizing the immersed feather in brine with a salinity from 4.0 to 6.0 for 10 minutes to 2 hours. (c) washing the feather with flowing water to remove impurities. (d) immersing and sterilizing the feather in 0.1~0.2 weight % (v/v) sodium chloride (NaCl) solution for 5 minutes to 1 hour (e) drying the feather at 15° C.~30° C. for 30 minutes to 72 hours. (f) sterilizing the dried feather by irradiating 10~400 nm UV for 10 minutes to 2 hours. (g) separating a calamus or a rachis from the sterilized feather. (h) sterilizing the separated calamus or rachis by irradiating 10~400 nm UV for 10 minutes to 2 hours. (i) cutting the sterilized calamus or rachis to 2~7 mm for easier grinding. (j) sterilizing the cut feather by irradiating 10~400 nm UV for 10 minutes to 2 hours. (k) grinding the cut and sterilized calamus or rachis (l) sterilizing the resulting powder by irradiating 10~400 nm UV for 10 minutes to 2 hours.

In the above preparation method, the water used for immersing and hydrating the feather is not particularly limited. Preferably, common tap water or distilled water may be used, and one having a temperature from 20° C. to 77° C. is preferable. If the water temperature exceeds 77° C., the epidermal tissue may be deformed. And, if the water temperature is below 20° C., hydration may be insufficient.

The immersing time may be controlled depending on the condition of the materials so as to attain sufficient hydration. Preferably, the immersing time may be from 1 minute to 2 hours. If the immersing time is less than 1 minute, hydration may be insufficient. And, an immersing time exceeding 2 hours is uneconomical and may result in deformation of tissues.

Meanwhile, Sterilization is performed in order to remove the saprophytes proliferating during the immersion from the feather. The sterilization method may be any one known in the art, as long as the feather is not deformed. Preferably, the feather is immersed in brine with a salinity from 4.0 to 6.0 for 10 minutes to 2 hours. Then, after removing the impurities, 1~2 g of NaCl in 1 L of water is added, and immersing and sterilization are carried out for 5 minutes to 1 hour. After completion of the immersion and prior to drying, the feather is washed using tap water or distilled water so as to remove remaining NaCl. The removal of impurities is performed by applying physical force after the feather is sufficiently hydrated by the immersion.

The method for drying the washed feather of birds is not particularly limited. Preferably, the feather is dried in a well ventilated place, out of the direct rays of the sun. Preferably, the feather is dried completely for 30 minutes to 72 hours at 15° C.~30° C., preferably at room temperature of about 25° C. Then, UV irradiation is carried out as described below.

The separation of the calamus and the rachis is performed as follows. The whole of the dried feather may be used. But, more preferably, the calamus portion with well-developed optical properties and multilayer structure and rich in keratin, and the rachis calamus rich in keratin and melanin pigments are screened out from the feather. From the dried feather, the portions other than the calamus and rachis portions, that is, barbs and vanes are completely removed (taken off) from the rachis by applying physical force. If the separated calamus or rachis is in bad condition or, if the lower portion of the calamus or the upper portion of the rachis is too thin, only the portions in good condition may be selected fro use. Then, UV irradiation is carried out as described below.

The whole of the separated feather or the selected calamus or rachis portion is ground into a powder using a grinding machine. If necessary, they may be cut finely (2~7 mm) in advance for easier grinding.

The resultant powder is sterilized using UV. UV with a wavelength of 10~400 nm is irradiated using a UV sterilizer without heat emission, at a distance of 10~50 cm from the powder. The irradiation time is not particularly limited, but 10 minutes to 2 hours is preferred.

The scale of fish, the scale transformed from the dermis, the degenerated or cornified variant of a scale, or the scale or horny scale of reptiles used to prepare the pharmaceutical composition of the present invention is not particularly limited. But, preferably, the scale of seawater fish having lots of scales, such as gray mullet, perch and rock trout, or freshwater fish having lots of scales, such as carp, crucian carp and trout, may be used. More preferably, the scale of gray mullet may be used. The reptiles are not particularly limited, but snake is preferred.

The scale of fish may be prepared by removing the scale from fish, followed by washing, and, preferably, powdering. The preparation method is not particularly limited, and may be comprises the steps of (a) immersing a fish in water of 20° C.~77° C. for 1 minute to 2 hours, and separating and washing a scale of the fish (b) immersing and sterilizing the scale washed in the step (a) in 0.1~0.2 weight % (w/v) NaCl solution for 5 minutes to 1 hour. (c) immersing and sterilizing the scale immersed in the step (b) in 1~3 weight % (v/v) vinegar solution for 15~20 minutes. (d) drying the scale immersed in the step (c) at 30° C.~70° C. for 5 minutes to 48 hours. (e) sterilizing the scale dried in the step (d) by irradiating with 10~400 nm UV for 10 minutes to 2 hours. (f) cutting the scale sterilized in the step (e) to 2~7 mm for easier grinding. (g) sterilizing the scale cut in the step (f) by irradiating with 10~400 nm UV for 10 minutes to 2 hours. (h) grinding the scale sterilized in the step (g) using a grinding machine. (i) sterilizing the powder resulting from the step (h) by irradiating with 10~400 nm UV for 10 minutes to 2 hours. The procedures for immersion, washing, drying, sterilization, and UV treatment are the same as described above.

And, the powder of the scale transformed from the dermis, the degenerated or cornified variant of a scale, or the scale or horny scale of reptiles may be prepared by the steps of: (a) applying Physical force to a dead body of fish or reptiles so as to separate the scale or skin; (b) sterilizing the separated scale or skin in brine with a salinity from 4.0 to 6.0 for 10 minutes to 2 hours; (c) immersing the scale or skin in 1~3% (v/v) vinegar solution for 10~20 minutes and sterilized; (d) washing the scale or skin with flowing water to remove impurities; (e) drying the washed scale or skin at 20° C.~70° C. for 5 minutes to 72 hours; (f) sterilizing the dried scale or skin by irradiating with 10~400 nm UV for 10 minutes to 2 hours; (g) cutting the scale or skin to 3~4 mm in width and length; (h) sterilizing the cut scale or skin by irradiating with 10~400 nm UV for 10 minutes to 2 hours; (i) grinding the scale or skin using a grinding machine; and (j) sterilizing the resulting powder by irradiating with 10~400 nm UV for 10 minutes to 2 hours. The procedures for immersion, washing, drying, sterilization, and UV treatment are the same as described above.

The anticancer pharmaceutical composition of the present invention may be prepared by mixing the aforesaid ingredients. Preferably, 70~85 weight % of the feather of birds may be mixed with 15~30 weight % of the scale of fish, the scale transformed from the dermis, the degenerated or cornified variant of a scale, or the scale or horny scale of reptiles. More preferably, 80 weight % of the feather of birds may be mixed with 20 weight % of the scale of fish, the scale transformed from the dermis, the degenerated or cornified variant of a scale, or the scale or horny scale of reptiles.

In one examples of the present invention, calamus and rachises of chicken, duck, turkey and goose were used as the feather of birds, and they were mixed with the powder of the scale of fish, the scale transformed from the dermis, the degenerated or cornified variant of a scale, or the scale or horny scale of reptiles in order to prepare the inventive compositions.

In one test example of the present invention, the inventive composition was administered to a nude mouse to which colon cancer cells had been transplanted, in order to confirm the anticancer effect. Then, the effect of inhibiting the cancer cells was measured. As a result, about 60% or more cancer cell growth inhibition effect was confirmed, as compared to the control group to which nothing was administered.

Accordingly, the present invention provides a pharmaceutical composition for preventing and treating cell proliferative diseases which is able to inhibit and prevent the growth of cancer cells.

The pharmaceutical composition according to the present invention may comprise the material prepared by the present invention singly with a pharmaceutically effective amount or may further comprise at least one pharmaceutically acceptable carrier. As used herein, the term "pharmaceutically effective amount" refers to an amount resulting in a better effect as compared to the control group and, preferably, an amount effective in treating or preventing cell proliferative diseases.

The pharmaceutically effective amount of the pharmaceutical composition according to the present invention may be 10~1000 mg/day/kg body weight, preferably 150~600 mg/day/kg body weight. However, the pharmaceutically effective amount may be varied adequately, depending on various factors, including particular disease and severity thereof, age, body weight, physical condition and sex of the patient, administration route, period of treatment, and the like.

The diseases to which the pharmaceutical composition of the present invention can be applied are immunodeficiency-related diseases and cell proliferative diseases. The cell proliferative diseases are neoplastic diseases caused by tumors, and may be, for example, cancer diseases. The cancer diseases include, although not limited thereto, large intestine cancer, spleen cancer, colon cancer, lung cancer, liver cancer, stomach cancer, esophageal cancer, pancreatic cancer, gallbladder cancer, kidney cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, lymphoma, bone cancer, soft tissue sarcoma, spinal cancer, and the like.

As used herein, the phrase "pharmaceutically acceptable" refers that the carrier is physiologically acceptable, does not inhibit the action of the active ingredient when administered to human, and is non-toxic without allergic reactions such as gastroenteric trouble and dizziness or other adverse reactions. The carrier includes all types of solvent, dispersive medium, oil-in-water or water-in-oil emulsion, aqueous composition, liposome, microbead and microsome.

Meanwhile, the pharmaceutical composition according to the present invention may be formulated along with an adequate carrier depending on the administration route. No particular limitation is imposed on the administration route of the inventive pharmaceutical composition, but it may be administered orally.

In case the pharmaceutical composition of the present invention is administered orally, the pharmaceutical composition of the present invention may be formulated along with an adequate carrier for oral administration into powder, granule, tablet, pill, sugarcoated tablet, capsule, liquid, gel, syrup, suspension, wafer, or the like by a method known in the art. Examples of the adequate carrier may include a saccharide such as lactose, dextrose, sucrose, sorbitol, mannitol, xylitol, erythritol, maltitol, etc., a starch such as corn starch, wheat starch, rice starch, potato starch, etc., a cellulose such as cellulose, methylcellulose, sodium carboxymethylcellulose, hydroxypropylmethylcellulose, etc., and a filler such as gelatin, polyvinylpyrrolidone, etc. Further, crosslinked polyvinylpyrrolidone, agar, alginic acid, sodium alginate, etc. may be added as disintegrant. In addition, the pharmaceutical composition may further comprise an anticoagulant, a surfactant, a wetting agent, a fragrance, an antiseptic, or the like.

Besides, those described in the following literature may be used as the pharmaceutically acceptable carrier: Remington's Pharmaceutical Sciences, 19th ed., Mack Publishing Company, Easton, Pa., 1995.

Further, the pharmaceutical composition according to the present invention may comprise at least one buffer (e.g., saline or PBS), carbohydrate (e.g., glucose, mannose, sucrose or dextran), antioxidant, bacteriostat, chelating agent (e.g., EDTA or glutathione), adjuvant (e.g., aluminum hydroxide), suspension agent, thickener and/or preservative.

And, the pharmaceutical composition of the present invention may be prepared into a formulation which can provide immediate, sustained or delayed release of the active ingredient after being administered to a mammal by a method known in the art.

Further, the pharmaceutical composition of the present invention may be administered in combination with a compound known to have an effect of preventing or treating cancer diseases.

Further, the present invention provides a method for preparing a powder of a feather of birds. As describe above, the preparation method comprises the steps of: (a) immersing a feather of birds in water of 20° C.~77° C. for 1 minute to 2 hours; (b) sterilizing the immersed feather in brine with a salinity from 4.0 to 6.0 for 10 minutes to 2 hours; (c) washing the feather well with flowing water to remove impurities; (d) immersing the feather in 0.1~0.2 weight % (v/v) NaCl solution for 5 minutes to 1 hour and sterilizing the same; (e) drying the feather at 15° C.~30° C. for 30 minutes to 72 hours; (f) sterilizing the dried feather by irradiating with 10~400 nm UV for 10 minutes to 2 hours; (g) separating a calamus or a rachis from the sterilized feather; (h) sterilizing the separated calamus or rachis by irradiating with 10~400 nm UV for 10 minutes to 2 hours; (i) cutting the sterilized calamus or rachis to 2~7 mm for easier grinding; (j) sterilizing the cut feather by irradiating with 10~400 nm UV for 10 minutes to 2 hours; (k) grinding the cut and sterilized calamus or rachis; and (l) sterilizing the resulting powder by irradiating with 10~400 nm UV for 10 minutes to 2 hours. The procedures for immersion, washing, drying, sterilization, and UV treatment are the same as described above.

Further, the present invention provides a method for preparing a powder of a scale of fish. As describe above, the preparation method comprises the steps of: (a) immersing a fish in water of 20° C.~77° C. for 1 minute to 2 hours and separating and washing a scale of the fish; (b) immersing and sterilizing the scale washed in the step (a) in 0.1~0.2 weight % (w/v) NaCl solution for 5 minutes to 1 hour; (c) immersing and sterilizing the scale immersed in the step (b) in 1~3 weight % (v/v) vinegar solution for 15~20 minutes; (d) drying the scale immersed in the step (c) at 30° C.~70° C. for 5 minutes to 48 hours; (e) sterilizing the scale dried in the step (d) by irradiating with 10~400 nm UV for 10 minutes to 2 hours; (f) cutting the scale sterilized in the step (e) to 2~7 mm for easier grinding; (g) sterilizing the scale cut in the step (f) by irradiating with 10~400 nm UV for 10 minutes to 2 hours; (h) grinding the scale sterilized in the step (g) using a grinding machine; and (i) sterilizing the powder resulting from the step (h) by irradiating with 10~400 nm UV for 10 minutes to 2 hours. The procedures for immersion, washing, drying, sterilization, and UV treatment are the same as described above.

The present invention further provides a method for preparing a powder of a scale transformed from the dermis, or the like. As describe above, the preparation method comprises the steps of: (a) separating a scale transformed from the dermis, the degraded or cornified variant of a scale, or the scale or horny scale of reptiles from a dead body by applying physical force; (b) sterilizing the separated scale or skin in brine with a salinity from 4.0 to 6.0 for 10 minutes to 2 hours; (c) immersing and sterilizing the scale or skin in 1~3% (v/v) vinegar solution for 10~20 minutes; (d) washing the scale or skin with flowing water to remove impurities; (e) drying the washed scale or skin at 20° C.~70° C. for 5 minutes to 72 hours; (f) sterilizing the dried scale or skin by irradiating with 10~400 nm UV for 10 minutes to 2 hours; (g) cutting the scale or skin to 3~4 mm in width and length; (h) sterilizing the cut scale or skin by irradiating with 10~400 nm UV for 10 minutes to 2 hours; (i) grinding the scale or skin using a grinding machine; and (j) sterilizing the resulting powder by irradiating with 10~400 nm UV for 10 minutes to 2 hours. The procedures for immersion, washing, drying, sterilization, and UV treatment are the same as described above.

The aforesaid preparation methods may further comprise the steps of: sterilizing using brine with a salinity from 4.0 to 6.0 and 3% (v/v) vinegar solution; and sterilizing by irradiating with 10~400 nm UV for 10 minutes to 2 hours.

The present invention further provides a method for oral administration of the inventive composition. The components of the inventive composition are the same as described above, and the method for oral administration may be one known in the art.

MODE FOR INVENTION

Hereinafter, the present invention is described in more detail through examples.

However, the following examples are provided for illustrative purposes only, and they are not intended to limit the present invention.

Example 1: Preparation of Inventive Composition 1-1. Preparation of Powder of Bird (Chicken) Feather A chicken feather was immersed in water of 77° C. for 20 minutes, and then in brine with a salinity of 4 for 30 minutes. After washing well with flowing water, the feather was immersed in 0.1% NaCl solution for 10 minutes and impurities were removed. Subsequently, the feather was dried for 48 hours at room temperature, in a well ventilated place. The dried feather was irradiated with UV for 1 hour, using a UV lamp (Birtcher, U.S.; no heat emission type) at a distance of 30 cm from the feather. Other portions excluding the calamus or the rachis were removed by applying physical force (with hand). After irradiating with UV for 1 more hour, using a UV lamp at a distance of 30 cm, they were cut to a size of about 5 mm using a cutter. After irradiating with UV for 1 hour, using a UV lamp at a distance of 30 cm, followed by grinding using a grinding machine, a powder of chicken feather was prepared by irradiating the resulting powder with UV for 1 hour, using a UV lamp at a distance of 30 cm.

1-2. Preparation of Scale Powder

A dead body of gray mullet was immersed in water of 50° C. for 20 minutes. The outer surface was cleaned using a soft scrubber (or brush) and physical force was applied to separate the scale. The separated scale was washed well and immersed in 0.1 weight % (w/v) brine for 10 minutes, and then in 1 weight % (v/v) vinegar solution for 20 minutes. Then, impurities were completely removed by washing well with flowing water. The scale was completely dried at room temperature (about 25° C.) for 24 hours. Then, UV was irradiated for 1 hour, using a UV lamp at a distance of 30 cm from the scale. After cutting to about 5 mm using a cutter, UV was irradiated for 1 hour. After grinding using a grinding machine, a scale powder was prepared by irradiating the resulting powder with UV for 1 hour, using a UV lamp at a distance of 30 cm.

Also, the skin was separated from the scale, skin or horny scale of a dead body of reptiles. The separated skin was immersed in brine with a salinity of 4.0 for minutes. After washing well with flowing water, the skin was immersed in 1 weight % (v/v) vinegar solution for 20 minutes. Then, impurities were completely removed by washing well with flowing water. After drying at room temperature for 48 hours, in a well ventilated place, UV was irradiated for 1 hour, using a UV lamp at a distance of 30 cm. After cutting to about 3~4 mm using a cutter, UV was irradiated for 1 hour at a distance of 30 cm. After grinding using a grinding machine, a scale powder was prepared by irradiating the resulting powder with UV for 1 hour, using a UV lamp at a distance of 30 cm.

1-3. Preparation of Inventive Composition

The feather powder of chicken and the scale powder of gray mullet prepared in Examples 1~1 and 1~2 were mixed at a proportion of 80 weight % and 20 weight %, respectively, to prepare an anticancer composition of the present invention.

Example 2: Preparation of Inventive Composition

A composition of the present invention was prepared in the same manner as in Example 1-3, except for using a feather of duck in Example 1-1.

Example 3: Preparation of Inventive Composition

A composition of the present invention was prepared in the same manner as in Example 1-3, except for using a feather of turkey in Example 1-1.

Example 4: Preparation of Inventive Composition

A composition of the present invention was prepared in the same manner as in Example 1-3, except for using a feather of goose in Example 1-1.

Test Example: Measurement of Anticancer Effect of Inventive Anticancer Composition The anticancer effect of the inventive composition was tested at the Chemon Preclinical Research Center (approved by the KGLP) using a nude mouse transplanted with human colon cancer cells.

7-weeks-old specific pathogen free (SPF) athymic BALB/C nude mice (SLC Japan, Japan) were weighed and grouped to 6 groups, 10 per each group, as follows: negative control group (1), positive control group (1) and test groups (4). The mice were identified by the identification label of the cage and using ear punching.

The test groups were designed as in Table 1.

TABLE 1

| Group | Sex | Number (heads) | Animal No. | Administration amount (mg/kg) | Number of administrations (time/day) |
|---|---|---|---|---|---|
| G1 | female | 10 | 1~10 | 0 | 2 |
| G2 | female | 10 | 11~20 | 2 | 0.5 |
| G3 | female | 10 | 21~30 | 75 | 2 |
| G4 | female | 10 | 31~40 | 150 | 2 |
| G5 | female | 10 | 41~50 | 300 | 2 |
| G6 | female | 10 | 51~60 | 300 | 2 |

G1: negative control group (excipient)
G2: positive control group (abdominal administration of positive control substance once in 2 days)
G3~G6: test substance administration groups (for G6, test substance had been administered for 3 weeks prior to transplantation of colon cancer cells)

Colon cancer cells (HCT15) were thawed in a constant-temperature water bath of 371° C. as soon as possible. After mixing well with 10 mL of RPMI1640 culture medium (Sigma Aldrich, USA), centrifuge was performed at 1000 rpm for 10 minutes. The resulting cell pellet was mixed well with 5 mL of RPMI1640 culture medium containing 10% fetal bovine serum (FBS), and the cells were cultured in a cell culture flask under the condition of 37° C. and 5% $CO_2$. The cultured cancer cells were suspended in physiological saline to a concentration of $1\times10^7$ cells/mL and transplanted subcutaneously to the mice, 0.3 mL ($3\times10^6$ cells) each.

The composition prepared in Example 1 was suspended at various concentrations in sterilized, distilled water for injection (Choongwae Pharma Corporation, Korea) as excipient, ground using a grinding machine (homogenizer), and orally administered to the mice at a dose of 75 mg/kg body weight (G3), 150 mg/kg body weight (G4) or 300 mg/kg body weight (G5), respectively, for 3 weeks, twice a day. Of the test groups, the pre-administration group (G6) had been orally administered with the composition at a dose of 300 mg/kg body weight for 3 weeks, twice a day, before the transplantation of the cancer cells. Following the transplantation of the cancer cells, they were administered in the same way for 3 weeks.

In the negative control group (G1), the excipient was orally administered for 3 weeks, twice a day, instead of the inventive anticancer composition. In the positive control group (G2), doxorubicin was abdominally administered at a dose of 2 mg/kg body weight for 3 weeks, once in 2 days, instead of the inventive anticancer composition. The doxorubicin solution was prepared by dissolving in the excipient by a method known in the art.

During the test, the mice were kept under the condition of 23±3° C. and relative humidity of 55±15%, and access to water and feed was allowed freely.

Tumor volume was measured on days 12, 15, 19 and 22 after the inoculation of the cancer cells. Length, width and height of the tumor were measured using a vernier caliper, and the tumor volume was calculated by the following equation:

$$\text{Tumor volume} = (\text{Length} \times \text{Width} \times \text{Height}) \div 2$$

The tumor volume measurement result is given in Table 2 (unit: $mm^3$).

TABLE 2

|  | Day 12 | Day 15 | Day 19 | Day 22 |
|---|---|---|---|---|
| G1 | 48.2 ± 21.9 | 141.1 ± 39.0 | 289.0 ± 102.8 | 704.6 ± 212.4 |
| G2 | 29.3 ± 16.0 | 93.7 ± 65.9 | 149.0 ± 77.6 | 258.6 ± 160.1 |
| G3 | 32.2 ± 27.0 | 100.5 ± 56.9 | 172.2 ± 71.9 | 251.9 ± 108.8 |
| G4 | 53.0 ± 29.1 | 104.2 ± 63.4 | 177.2 ± 106.4 | 235.3 ± 109.3 |
| G5 | 33.1 ± 24.4 | 90.4 ± 51.6 | 180.3 ± 84.7 | 232.1 ± 121.7 |
| G6 | 34.5 ± 28.9 | 96.6 ± 55.8 | 193.6 ± 78.6 | 214.2 ± 64.8 |

On days 19 and 22, statistically significant ($p<0.05$) decrease of tumor volume was observed in all the test groups (G3~G6) to which the inventive composition was administered, as compared to the negative control group (G1). On day 22 (when autopsy was carried out), the groups G3~G6 showed tumor inhibition effects ([1−(tumor volume of administered group/tumor volume of negative control group)]×100(%)) of 64.3%, 66.6%, 67.1% and 69.6%, respectively. They were superior to that of the doxorubicin administered group (G2; 59.5%).

Abnormal symptoms related with the administration of the inventive composition were not observed, and no significant change in body weight was observed, as shown in Table 3 (unit: g).

TABLE 3

|    | Day 4         | Day 11        | Day 18        | Day 21        |
|----|---------------|---------------|---------------|---------------|
| G1 | 19.93 ± 1.67  | 19.68 ± 1.53  | 19.80 ± 1.17  | 18.92 ± 1.29  |
| G2 | 20.57 ± 0.99  | 20.51 ± 0.85  | 19.87 ± 0.99  | 18.85 ± 1.04  |
| G3 | 20.58 ± 1.06  | 20.33 ± 1.08  | 19.94 ± 1.21  | 19.41 ± 1.48  |
| G4 | 19.85 ± 0.51  | 19.90 ± 0.57  | 19.74 ± 0.49  | 19.26 ± 0.64  |
| G5 | 20.11 ± 1.49  | 19.93 ± 1.46  | 19.90 ± 1.54  | 19.11 ± 1.59  |
| G6 | 19.68 ± 0.82  | 19.86 ± 0.50  | 19.72 ± 0.85  | 19.16 ± 0.74  |

From the above, it can be confirmed that the composition according to the present invention is effective in inhibiting the proliferation of tumor cells.

Preparation Example: Preparation of Capsule Comprising Inventive Composition 100.0 mg of the composition prepared in Example 1, 83.0 mg of cornstarch, 175.0 mg of lactose and 2.0 mg of magnesium stearate were mixed homogeneously, and filled in a gelatin capsule, so that the weight of the contents per one capsule was 360 mg.

INDUSTRIAL APPLICABILITY

As can be seen from the foregoing, the inventive composition for preventing and treating cell proliferative diseases has the effect of inhibiting and preventing growth of cancer cells. Accordingly, the inventive composition for preventing and treating cell proliferative diseases may be used for anticancer purposes to prevent, ameliorate or treat cancer.

The invention claimed is:

1. A method for treating cell proliferative diseases comprising administering to a subject in need thereof a composition comprising 70~85 weight % of a feather of bird and 15~30 weight % of a scale of fish as an active ingredient, wherein the feather of bird is a powder of whole feather, calamus or rachis, and further wherein the powder of the calamus or rachis is prepared by a method comprising the steps of:
   (a) immersing a feather of birds in water of 20° C.~77° C. for 1 minute to 2 hours;
   (b) sterilizing the immersed feather in brine with a salinity from 4.0 to 6.0 for 10 minutes to 2 hours;
   (c) washing the feather with flowing water to remove impurities;
   (d) immersing and sterilizing the feather in 0.1~0.2 weight % (v/v) sodium chloride (NaCl) solution for 5 minutes to 1 hour;
   (e) drying the feather at 15° C.~30° C. for 30 minutes to 72 hours;
   (f) sterilizing the dried feather by irradiating 10~400 nm UV for 10 minutes to 2 hours;
   (g) separating a calamus or a rachis from the sterilized feather;
   (h) sterilizing the separated calamus or rachis by irradiating 10~400 nm UV for 10 minutes to 2 hours;
   (i) cutting the sterilized calamus or rachis to 2~7 mm for easier grinding;
   (j) sterilizing the cut feather by irradiating 10~400 nm UV for 10 minutes to 2 hours;
   (k) grinding the cut and sterilized calamus or rachis; and
   (l) sterilizing the resulting powder by irradiating 10~400 nm UV for 10 minutes to 2 hours.

2. The method according to claim 1, wherein the composition further comprises a scale transformed from the dermis, a degenerated or cornified variant of a scale, or a scale or horny scale of reptiles as an active ingredient.

3. The method of claim 1, wherein the bird is selected from the group consisting of chicken, duck, turkey, goose and ostrich.

4. A method for treating cell proliferative diseases comprising administering to a subject in need thereof a composition comprising 70~85 weight % of a feather of bird and 15~30 weight % of a scale of fish as an active ingredient, wherein a scale of fish is prepared by a method comprising the steps of:
   (a) immersing a fish in water of 20° C.~77° C. for 1 minute to 2 hours, and separating and washing a scale of the fish;
   (b) immersing and sterilizing the scale washed in the step (a) in 0.1~0.2 weight % (w/v) NaCl solution for 5 minutes to 1 hour;
   (c) immersing and sterilizing the scale immersed in the step (b) in 1~3 weight % (v/v) vinegar solution for 15~20 minutes;
   (d) drying the scale immersed in the step (c) at 30° C.~70° C. for 5 minutes to 48 hours;
   (e) sterilizing the scale dried in the step (d) by irradiating with 10~400 nm UV for 10 minutes to 2 hours;
   (f) cutting the scale sterilized in the step (e) to 2~7 mm for easier grinding;
   (g) sterilizing the scale cut in the step (f) by irradiating with 10~400 nm UV for 10 minutes to 2 hours;
   (h) grinding the scale sterilized in the step (g) using a grinding machine; and
   (i) sterilizing the powder resulting from the step (h) by irradiating with 10~400 nm UV for 10 minutes to 2 hours.

5. The method of claim 1, wherein the fish is selected from the group consisting of gray mullet, perch and rock trout, carp, crucian carp and trout.

6. The method of claim 1 wherein the cell proliferative disease is neoplastic disease caused by tumor.

7. The method of claim 6, wherein the neoplastic disease is cancer.

8. The method of claim 7, wherein the cancer is selected from the group consisting of large intestine cancer, spleen cancer, colon cancer, lung cancer, liver cancer, stomach cancer, esophageal cancer, pancreatic cancer, gallbladder cancer, kidney cancer, bladder cancer, prostate cancer, testicular cancer, cervical cancer, endometrial cancer, choriocarcinoma, ovarian cancer, breast cancer, thyroid cancer, brain cancer, head and neck cancer, malignant melanoma, lymphoma, bone cancer, soft tissue sarcoma, and spinal cancer.

9. A method for treating cell proliferative diseases comprising administering to a subject in need thereof a composition comprising 70~85 weight % of a feather of bird and 15~30 weight % of a scale of fish as an active ingredient, further wherein the composition further comprises a scale transformed from the dermis, a degenerated or cornified variant of a scale, or a scale or horny scale of reptiles as an active ingredient, wherein the scale transformed from the dermis, the degradated or cornified variant of a scale, or the scale or horny scale of reptiles is prepared by a method comprising the steps of:
- (a) applying physical force to a dead body of fish or reptiles so as to separate the scale or skin;
- (b) sterilizing the separated scale or skin in brine with a salinity from 4.0 to 6.0 for 10 minutes to 2 hours;
- (c) immersing the scale or skin in 1~3% (v/v) vinegar solution for 10~20 minutes and sterilizing;
- (d) washing the scale or skin with flowing water to remove impurities;
- (e) drying the washed scale or skin at 20° C.~70° C. for 5 minutes to 72 hours;
- (f) sterilizing the dried scale or skin by irradiating with 10~400 nm UV for 10 minutes to 2 hours;
- (g) cutting the scale or skin to 3~4 mm in width and length;
- (h) sterilizing the cut scale or skin by irradiating with 10~400 nm UV for 10 minutes to 2 hours;
- (i) grinding the scale or skin using a grinding machine; and
- (j) sterilizing the resulting powder by irradiating with 10~400 nm UV for 10 minutes to 2 hours.

10. The method of claim 2, wherein the reptile is a snake.

11. The method of claim 1, wherein the composition is administered orally.

12. The method of claim 4, wherein the composition further comprises a scale transformed from the dermis, a degenerated or cornified variant of a scale, or a scale or horny scale of reptiles as an active ingredient.

13. The method of claim 12, wherein the reptile is a snake.

14. The method of claim 9, wherein the reptile is a snake.

15. The method of claim 4, wherein the composition is administered orally.

16. The method of claim 9, wherein the composition is administered orally.

* * * * *